US009903815B2

(12) United States Patent
Lee et al.

(10) Patent No.: US 9,903,815 B2
(45) Date of Patent: Feb. 27, 2018

(54) AUTHENTICATION STRUCTURE/APPARATUS AND METHOD

(71) Applicant: SAMSUNG ELECTRONICS CO., LTD., Suwon-si (KR)

(72) Inventors: Jaesoong Lee, Suwon-si (KR); Jineun Kim, Suwon-si (KR); Younggeun Roh, Seoul (KR); Yeonsang Park, Seoul (KR); Changwon Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 121 days.

(21) Appl. No.: 14/881,878

(22) Filed: Oct. 13, 2015

(65) Prior Publication Data

US 2016/0103065 A1  Apr. 14, 2016

(30) Foreign Application Priority Data

Oct. 13, 2014 (KR) .................. 10-2014-0137850

(51) Int. Cl.
*G06K 9/74* (2006.01)
*G01N 21/55* (2014.01)
*G02B 6/26* (2006.01)
*G01N 21/552* (2014.01)
*G02B 6/122* (2006.01)
*G02B 27/48* (2006.01)
*F21V 8/00* (2006.01)

(52) U.S. Cl.
CPC ......... *G01N 21/553* (2013.01); *G02B 6/0043* (2013.01); *G02B 6/1226* (2013.01); *G02B 27/48* (2013.01)

(58) Field of Classification Search
CPC .... G01N 21/553; G02B 27/48; G02B 6/0043; G02B 6/1226; G02B 26/02; B42D 25/23; B42D 25/24; B42D 25/29; B42D 25/351; B42D 25/355; B42D 25/36; B42D 25/445; B42D 25/364; B32B 2255/20; B32B 2255/205; B32B 2307/20; B32B 2307/40; B82Y 20/00
USPC ............................................ 356/445; 385/38
See application file for complete search history.

(56) References Cited

U.S. PATENT DOCUMENTS 7,351,374 B2   4/2008   Stark
8,054,098 B2  11/2011   Koushanfar et al.
(Continued)

FOREIGN PATENT DOCUMENTS

KR   10-2010-0021446 A   2/2010
KR   10-2012-0075189 A   7/2012
WO      2006/021911 A1   3/2006

OTHER PUBLICATIONS

Ravikanth, "Physical One-Way Functions", Mar. 2001, 154 pages total, Massachusetts Institute of Technology, Massachusetts, USA.

(Continued)

*Primary Examiner* — Sunghee Y Gray
(74) *Attorney, Agent, or Firm* — Sughrue Mion, PLLC

(57) ABSTRACT

According to an aspect of an exemplary embodiment, an authentication apparatus for authenticating an object includes an input coupler configured to receive incident light and generate surface plasmons from the incident light; and an output coupler configured to output a speckle pattern based on the surface plasmons.

19 Claims, 12 Drawing Sheets

(56) References Cited

U.S. PATENT DOCUMENTS

| | | |
|---|---|---|
| 8,741,713 B2 | 6/2014 | Bruley et al. |
| 2009/0153841 A1 | 6/2009 | Ophey et al. |
| 2011/0026783 A1 | 2/2011 | Fujii et al. |
| 2012/0051691 A1* | 3/2012 | Zhang .................. G01C 19/721 385/14 |
| 2012/0168506 A1* | 7/2012 | Ruehrmair .............. G06F 21/73 235/454 |
| 2013/0266034 A1* | 10/2013 | Yu .......................... B82Y 20/00 372/27 |
| 2014/0085191 A1 | 3/2014 | Gonion et al. |
| 2015/0331185 A1* | 11/2015 | Park ....................... G02B 6/107 359/341.1 |
| 2016/0257160 A1* | 9/2016 | Firth ....................... B82Y 20/00 |

OTHER PUBLICATIONS

Yeh et al., "Robust laser speckle recognition system for authenticity identification", Optics Express, Oct. 10, 2012, 12 pages total, vol. 20 No. 22, Optical Society of America, Taiwan.

\* cited by examiner

< COMPARATIVE EXAMPLE >

AUTHENTICATION STRUCTURE/APPARATUS AND METHOD

RELATED APPLICATION

This application claims priority from Korean Patent Application No. 10-2014-0137850, filed on Oct. 13, 2014, in the Korean Intellectual Property Office, the disclosure of which is incorporated herein in its entirety by reference.

BACKGROUND

1. Field

Apparatuses and methods consistent with exemplary embodiments relate to authentication structures and methods of authenticating objects, and apparatuses using the authentication structures.

2. Description of the Related Art

A physical unclonable function (PUF) may be used for security purposes. For example, when a PUF is applied to a device (or a product), such as a smart card, a memory stick, a storage medium, or a chip, it may be practically impossible to duplicate the device incorporating the PUF.

A PUF is based on the concept that a slight difference that is caused during a process is used as an identity or identifier of an individual device. Specifically, when light is emitted to a token that is formed by randomly distributing glass beads, a unique pattern is created. Because tokens are generally formed by distributing glass beads, the glass beads are randomly arranged in all of the tokens, and thus it is physically impossible to form the same token. Different patterns are created from tokens, and thus unique identities of the tokens or products including the tokens are established, like human fingerprints. A process of verifying identity, for example using the token or human fingerprint, is referred to as authentication.

However, when authenticating a token that is formed by distributing glass beads, an image unfortunately varies according to a direction in which light is emitted to the token, position of the token, and position of a detector. Also, because the token has a large size, a relatively bulky measurement system is used for authentication. Accordingly, it is difficult to popularize or commercialize authentication using the PUF.

SUMMARY

According to an aspect of an exemplary embodiment, an authentication apparatus for authenticating an object includes an input coupler configured to receive incident light and generate surface plasmons from the incident light; and an output coupler configured to output a speckle pattern based on the surface plasmons.

The authentication apparatus may include: a waveguide configured to transmit to the output coupler the surface plasmons generated by the input coupler.

The authentication apparatus may include a layer structure, the layer structure being at least one among a single-layer structure or a multi-layer structure, wherein the input coupler may be provided in a first area of the layer structure and the output coupler may be provided in a second area of the layer structure.

The first area and the second area may be apart from each other in an in-plane direction of the layer structure.

The input coupler may include at least one of a slit and a slot, and at least one of the slit and the slot may be formed in the first area of the layer structure.

The output coupler may include an optical scatterer formed in the second area of the layer structure.

The optical scatterer may include at least one among a slit, a slot, a spherical element, and a rod-type element, configured to scatter light.

The optical scatterer may include a plurality of scattering elements, each scattering element of the plurality of scattering elements being a nanoscale size or a microscale size.

The authentication apparatus may include a metal film, wherein the input coupler may be provided in a first area of the metal film, and the output coupler may be provided in a second area of the metal film.

The authentication apparatus may include a multi-layer structure comprising a metal film and a dielectric film, wherein the input coupler may be provided in a first area of the multi-layer structure, and the output coupler may be provided in a second area of the multi-layer structure.

The dielectric film may be formed on the metal film and may be configured to protect the metal film.

The authentication apparatus may include a multi-layer structure comprising a first metal film, a second metal film, and a dielectric film disposed between the first metal film and the second metal film, wherein the input coupler may be provided in a first area of the multi-layer structure, and the output coupler may be provided in a second area of the multi-layer structure.

The dielectric film and the second metal film may be sequentially disposed on the first metal film, wherein the input coupler may be formed in at least one among the first metal film and the dielectric film.

The authentication apparatus may include a multi-layer structure comprising a first dielectric film, a second dielectric film, and a metal film disposed between the first dielectric film and the second dielectric film, wherein the input coupler may be provided in a first area of the multi-layer structure and the output coupler may be provided in a second area of the multi-layer structure.

The authentication apparatus may be formed on the object. In this case, a substrate may be further provided between the authentication apparatus and the object.

An authentication system may include the authentication apparatus disposed on the object; and an optical pickup corresponding to the authentication apparatus, the optical pickup being configured to detect the speckle pattern.

The optical pickup may include: a light source configured to emit light to the input coupler of the authentication apparatus; and a detector configured to detect the speckle pattern output from the output coupler of the authentication apparatus.

The input coupler may be positioned to receive the light emitted from the light source, and the output coupler may be positioned to output the speckle pattern to the detector.

The input coupler may be positioned on a first surface of the authentication apparatus, and the output coupler may be positioned on a second surface of the authentication apparatus, the second surface being opposite from the first surface.

The light source may include a laser source.

According to another aspect of an exemplary embodiment, an apparatus includes an authentication structure configured to authenticate an object, wherein the authentication structure includes an input coupler, an output coupler spaced apart from the output coupler, and a waveguide disposed between the input coupler and the output coupler, wherein the output coupler may be configured to output an interference pattern produced by coherent waves that are guided along the waveguide from the input coupler to the output coupler.

The coherent waves may include surface plasmons.

The interference pattern may include a speckle pattern.

The authentication structure may include a layer structure, the layer structure being at least one among a single-layer structure or a multi-layer structure, wherein the input coupler may be provided in a first area of the layer structure and the output coupler may be provided in a second area of the layer structure.

According to a further exemplary embodiment, a method of authenticating an object includes generating a speckle pattern based on surface plasmons; detecting the speckle pattern; and authenticating the object based on the speckle pattern.

The authentication method may be performed with an authentication structure including an input coupler an output coupler, and a waveguide disposed between the input coupler and the output coupler.

The authentication method may include: generating the surface plasmons by using the input coupler; detecting the speckle pattern output from the output coupler based on the surface plasmons.

The generating of the surface plasmons by using the input coupler may include emitting light to the input coupler.

According to a still further aspect of an exemplary embodiment, a method of providing an authentication pattern includes receiving light at an input angle; generating surface plasmons from the received light; and outputting an authentication pattern based on the surface plasmons, wherein the authentication pattern is a speckle pattern, the speckle pattern remaining uniform when the input angle changes.

The method may include receiving first incident light at a first angle; generating first surface plasmons from the first incident light; outputting a first authentication pattern based on the first surface plasmons; receiving second incident light at a second angle different from the first angle; generating second surface plasmons from the second incident light; and outputting a second authentication pattern based on the second surface plasmons, wherein the first authentication pattern is identical to the second authentication pattern.

BRIEF DESCRIPTION OF THE DRAWINGS

The above and other aspects of the exemplary embodiments will become apparent and more readily appreciated from the following description of the exemplary embodiments, taken in conjunction with the accompanying drawings in which.

DETAILED DESCRIPTION

Figure 1:
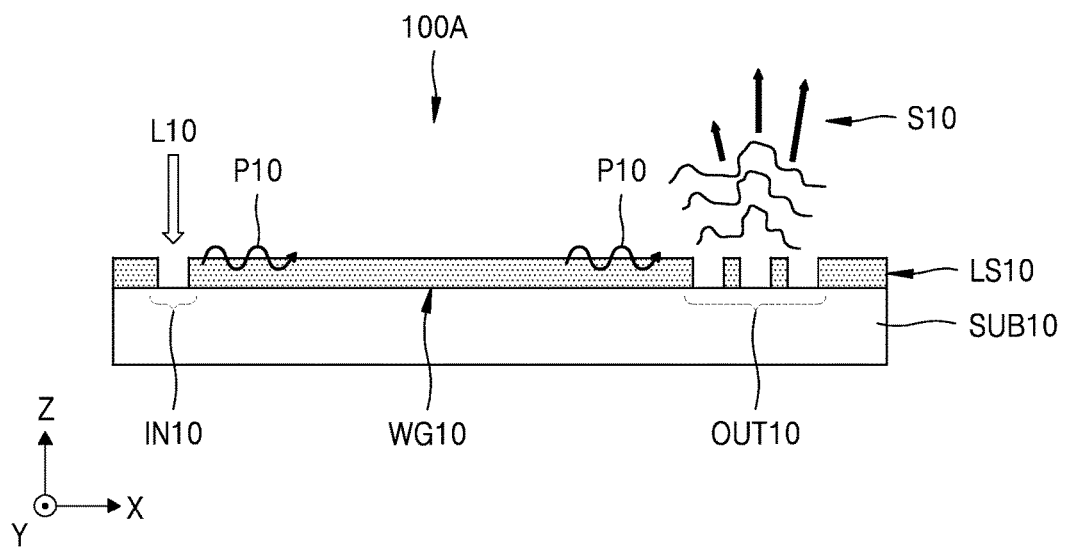
FIG. 1 is a cross-sectional view illustrating an authentication structure for authenticating an object, according to an exemplary embodiment.

Various exemplary embodiments will now be more fully described with reference to the accompanying drawings in which exemplary embodiments are shown.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular exemplary embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Exemplary embodiments are described herein with reference to cross-sectional illustrations that are schematic illustrations of idealized exemplary embodiments (and intermediate structures) of example embodiments. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Reference will now be made in detail to exemplary embodiments, examples of which are illustrated in the accompanying drawings. In the accompanying drawings, widths and thicknesses of layers and regions are exaggerated for clarity. In the detailed description, the same reference numerals generally denote the same elements.

As used herein, the term "and/or" includes any and all combinations of one or more of the associated listed items. Expressions such as "at least one of," when preceding a list of elements, modify the entire list of elements and do not modify the individual elements of the list.

FIG. 1 is a cross-sectional view illustrating an authentication structure 100A for authenticating an object, according to an exemplary embodiment. The authentication structure 100A may be referred to as an authentication token, a physical unclonable function (PUF) token, or a PUF structure. Also, the authentication structure 100A may be referred to as an optical authentication structure. Also, the authentication structure 100A may be referred to as a security device.

Referring to FIG. 1, the authentication structure 100A may be configured to output a speckle pattern S10 produced by surface plasmons P10. An identity of the object including the authentication structure 100A may be verified by detecting the speckle pattern S10. In other words, the speckle pattern S10 may be used to authenticate the object, which will be explained below in detail.

The authentication structure 100A may include an input coupler IN10 and an output coupler OUT10. The input coupler IN10 may function to generate the surface plasmons P10 using incident light L10. In some exemplary embodiments, the input coupler may include an interface element which may generate surface plasmons P10. The incident light L10 may be coherent light. For example, the incident light L10 may be laser light. The output coupler OUT10 may function to generate/output the speckle pattern S10 produced by the surface plasmons P10. That is, the speckle pattern S10 produced by the surface plasmons P10 may be generated and output by the output coupler OUT10. The authentication structure 100A may also include a waveguide WG10 that transmits (or guides) the surface plasmons P10 generated by the input coupler IN10 to the output coupler OUT10. The waveguide WG10 may be referred to as an optical waveguide, and may be disposed between the input coupler IN10 and the output coupler OUT10.

The authentication structure 100A may include a layer structure LS10 that is a single-layer or multi-layer structure. FIG. 1 illustrates a case in which the layer structure LS10 is a single-layer structure. The layer structure LS10 may be one metal film (or one metal slab). The layer structure LS10 may have a thickness ranging from, for example, several nanometers (nm) to several millimeters (mm), or a thickness ranging from, for example, tens of nm to hundreds of nm. When the layer structure LS10 is a metal, an air layer that contacts the layer structure LS10 may function as a dielectric layer. In some exemplary embodiments, a protective layer formed of a dielectric material may be further disposed on the layer structure LS10. The input coupler IN10 may be provided in a first area of the layer structure LS10 and the output coupler OUT10 may be provided in a second area of the layer structure LS10. The first area and the second area may be spaced apart from each other in an in-plane direction of the layer structure LS10, for example, in an X-axis direction of FIG. 1. In other words, the input coupler IN10 and the output coupler OUT10 may be spaced apart from each other in the in-plane direction of the layer structure LS10.

The input coupler IN10 may include at least one from among a slit or a slot that is formed in the first area of the layer structure LS10. At least one from among a slit or slot may be formed in the input coupler IN10. The terms 'slit' and 'slot' may each refer to a long narrow groove or opening. The slit and the slot used herein may be distinguished from each other by a size and a depth of a groove. For example, 'slit' may refer to a groove having a larger size and a greater depth than those of the 'slot'. However, there is no clear criterion for distinguishing the slit and the slot and the terms slit and the slot may be interchangeably used. The slit and the slot are an exemplary structure that may be included in the input coupler IN10. A configuration or a structure of the input coupler IN10 may be modified in various ways. Any desired structure that may generate the surface plasmons P10 by using the incident light L10 may be used for the input coupler IN10. For example, when the layer structure LS10 has a discontinuous area, the discontinuous area may be used as the input coupler IN10. Also, when the input coupler IN10 has an opening or a groove, a material may be filled in the opening or the groove. The material may be different from a material (e.g., a metal) of the layer structure LS10. Also, a structure, a size, and a pattern of the input coupler IN10 may be appropriately selected or optimized according to conditions (e.g., a wavelength and a frequency) of the incident light L10.

The output coupler OUT10 may include an optical scatterer that is formed in the second area of the layer structure LS10. The optical scatterer may include at least one selected from, for example, a slit, a slot, a spherical element, and a rod-type element. FIG. 1 illustrates a case in which a plurality of slits or slots are formed. However, a detailed structure of the optical scatterer is not limited to the slit, the slot, the spherical element, and the rod-type element and modifications may be made in various ways. A scale (e.g., a width or a size) of the slit, the slot, the spherical element, or the rod-type element of the optical scatterer may be a nanoscale size or a microscale size. When the optical scatterer includes a plurality of scattering elements, the plurality of scattering elements may each have a nanoscale size to a microscale size. The term "nanoscale size" used herein may refer to a size ranging from, for example, about 1 nm to hundreds of nm, and the term "microscale size" used herein may refer to a size ranging from, for example, about 1 micrometer (μm) to hundreds of μm. Also, the plurality of scattering elements may have random sizes and shapes, that is, non-uniform sizes and shapes. Also, when the output coupler OUT10 includes at least one opening or groove, a material may be filled in the at least one opening or groove. The material may be different from a material (e.g., a metal) of the layer structure LS10.

In the present exemplary embodiment, the authentication structure 100A may be disposed on a substrate SUB10. That is, the layer structure LS10 of the authentication structure 100A may be formed on the substrate SUB10. The substrate SUB10 may be a transparent substrate such as a glass or sapphire substrate, or may be a semi-transparent or opaque substrate. The substrate SUB10 may be considered a part of the authentication structure 100A. That is, the authentication structure 100A may include the substrate SUB10 and the layer structure LS10. However, without the substrate SUB10, the layer structure LS10, that is, the authentication structure 100A, may be formed directly on the object. In this case, the object may be a device or a product. In other words, the substrate SUB10 of FIG. 1 may be replaced by the object.

Figure 2:
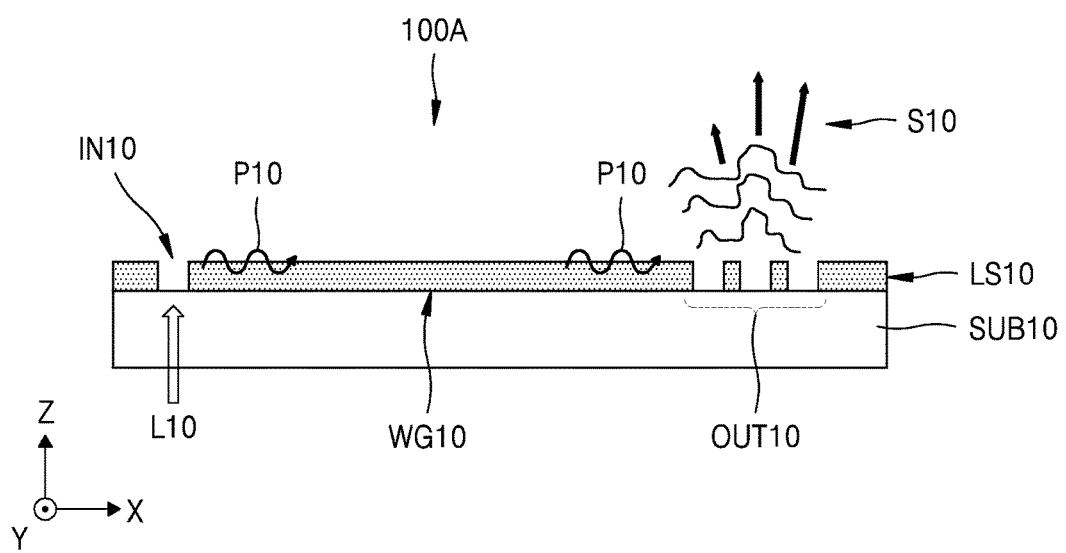
FIG. 2 is a cross-sectional view illustrating a case where a direction in which incident light is emitted in FIG. 1 is changed, according to an exemplary embodiment.

Although the incident light L10 is emitted from the top of the layer structure LS10 to the input coupler IN10 in FIG. 1, a direction in which the incident light L10 is emitted may be changed, as shown in FIG. 2.

Referring to FIG. 2, the incident light L10 may be emitted from the bottom of the layer structure LS10 to the input coupler IN10. In this case, the substrate SUB10 may be transparent or semi-transparent to the incident light L10.

In FIGS. 1 and 2, when the incident light L10 is emitted to the input coupler IN10, the surface plasmons P10 may be generated on a surface of the layer structure LS10 and may be transmitted to the output coupler OUT10. The incident light L10 may be coherent light and the surface plasmons P10 may be coherent waves. The surface plasmons P10 that are transmitted from the input coupler IN10 to the output coupler OUT10 may be converted into coherent electromagnetic waves by the output coupler OUT10 and may be emitted to the outside of the layer structure LS10. In this case, when the output coupler OUT10 includes a scatterer having a nanoscale size to a microscale size, the coherent electromagnetic wave may produce the speckle pattern S10.

The scatterer of the output coupler OUT10 may have a physical unclonable function (PUF), and the speckle pattern S10 may have a unique identity. Accordingly, the authentication structure 100A of FIGS. 1 and 2 may be used to authenticate the object, in a manner analogous to a human fingerprint.

Figure 3:
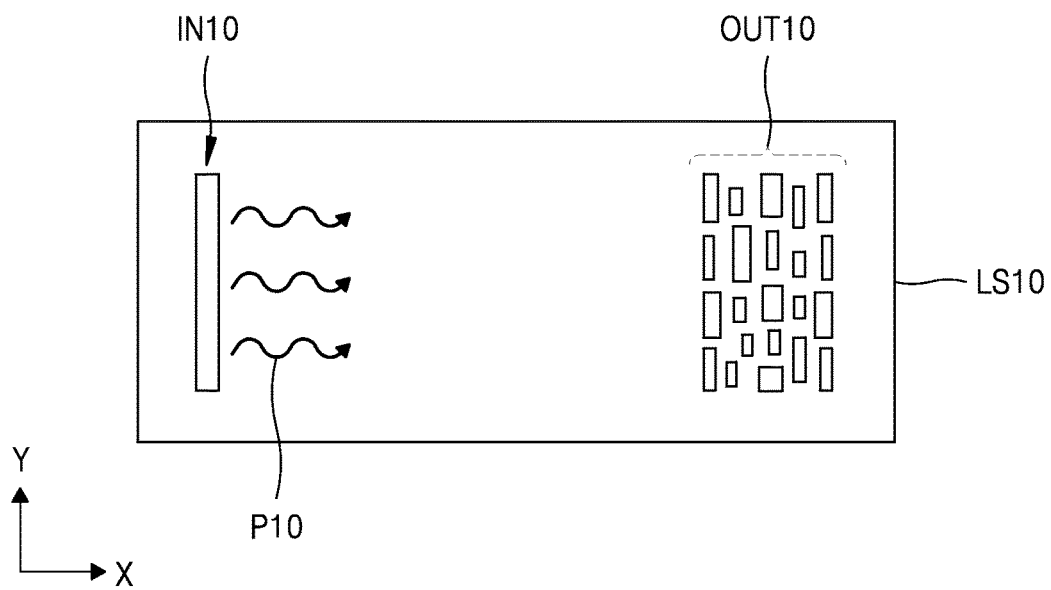
FIG. 3 is a plan view illustrating the authentication structure of FIG. 1, according to an exemplary embodiment.

FIG. 3 is a plan view illustrating the authentication structure 100A of FIG. 1, according to an exemplary embodiment.

Referring to FIG. 3, the input coupler IN10 may be provided in a first area of the layer structure LS10, and the output coupler OUT10 may be provided in a second area that is spaced apart from the first area. The input coupler IN10 may include, for example, at least one from among a slit or a slot. The output coupler OUT10 may include a plurality of scattering elements, and the plurality of scattering elements may be, for example, slits, slots, spherical elements, or rod-type elements. Although the output coupler OUT10 includes a plurality of slits and/or slots in FIG. 3, a detailed structure of the output coupler OUT10 may be modified in various ways. The authentication structure 100A of FIG. 3 is exemplary and various modifications may be made.

Figure 4:
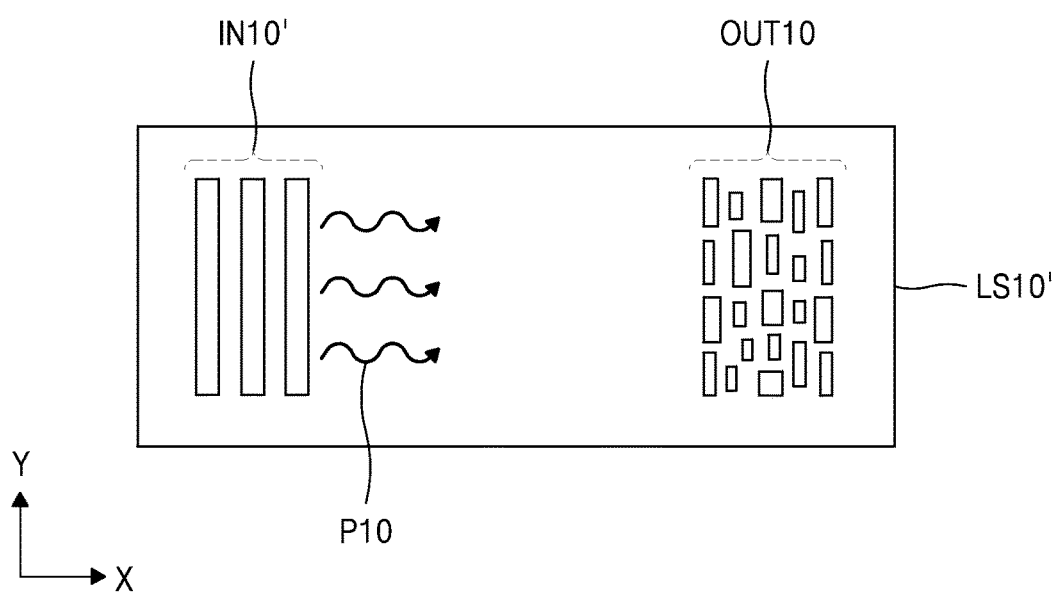
FIG. 4 is a plan view illustrating a modification of FIG. 3, according to an exemplary embodiment.

FIG. 4 illustrates a case where an input coupler IN10' includes a plurality of slits (or slots). The plurality of slits may have uniform shapes or non-uniform shapes. That is, a plurality of slits or slots having different shapes and sizes may be used as the input coupler IN10'. Also, a configuration of the input coupler IN10' may be modified in other various ways. In FIG. 4, reference numeral LS10' denotes a layer structure including the input coupler IN10' and the output coupler OUT10.

Figure 5:
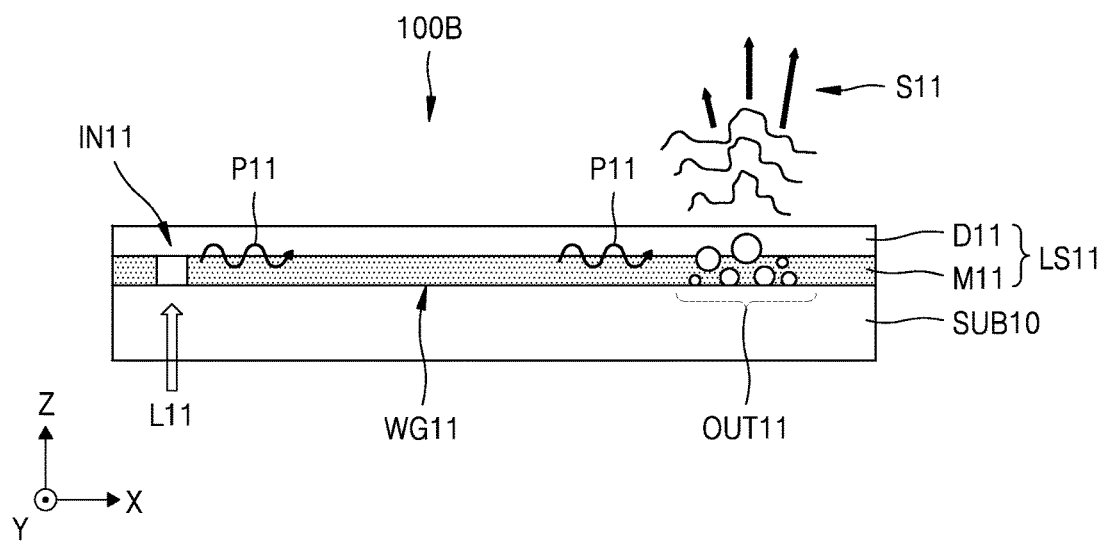
FIG. 5 is a cross-sectional view illustrating an authentication structure for authenticating an object, according to another exemplary embodiment.

FIG. 5 is a cross-sectional view illustrating an authentication structure 100B for authenticating an object, according to another exemplary embodiment.

Referring to FIG. 5, the authentication structure 100B may include a layer structure LS11 that is a multi-layer structure. The layer structure LS11 may include a metal film M11 and a dielectric film D11. The dielectric film D11 may be disposed on the metal film M11. The dielectric film D11 may cover a top surface of the metal film M11, and may function as a protective film for the metal film M11. The dielectric film D11 may prevent the metal film M11 from being eroded and damaged. The dielectric film D11 may be a final layer of the authentication structure 100B.

An input coupler IN11 may be provided in a first area of the layer structure LS11 and an output coupler OUT11 may be provided in a second area of the layer structure LS11. The input coupler IN11 may include, for example, at least one from among a slit or a slot that is formed in the metal film M11. The output coupler OUT11 may include an optical scatterer that is formed in at least one selected from the metal film M11 and the dielectric film D11. The output coupler OUT11 includes a plurality of spherical elements in FIG. 5. In this case, the plurality of spherical elements may have non-uniform sizes and may be randomly arranged. A portion of the layer structure LS11 between the input coupler IN11 and the output coupler OUT11 may be a waveguide WG11.

When incident light L11 is emitted to the input coupler IN11, surface plasmons P11 may be generated in the input coupler IN11 due to the incident light L11, and may be transmitted to the output coupler OUT11 through the waveguide WG11. A speckle pattern S11 may be generated and output by the output coupler OUT11 due to the surface plasmons P11. The incident light L11 may be coherent light, for example, laser, and the surface plasmons P11 may be coherent waves. Because the metal film M11 and the dielectric film D11 are used in the present exemplary embodiment, the surface plasmons P11 may be transmitted through an interface between the metal film M11 and the dielectric film D11, thereby improving surface plasmon transmission efficiency.

Configurations of the input coupler IN11 and the output coupler OUT11 of FIG. 5 are exemplary and various modifications may be made. For example, the input coupler IN11 may be formed in the dielectric film D11 instead of the metal film M11, or may be formed in both the metal film M11 and the dielectric film D11. Also, when the input coupler IN11 includes an opening or a groove such as a slit or a slot, a material may be filled in the opening or the groove. For example, when an opening or a groove is formed in the metal film M11, a material (e.g., a dielectric material) having a refractive index different from that of a material of the metal film M11 may be filled in the opening or the groove. When an opening or a groove is formed in the dielectric film D11, a material having a refractive index different from that of a material of the dielectric film D11 may be filled in the opening or the groove. The output coupler OUT11 may be formed in any one selected from the metal film M11 and the dielectric film D11, and may include elements (e.g., slits, slots, or rod-type elements) other than the spherical elements, or a combination thereof. Also, although the incident light L11 is emitted from the bottom of the layer structure LS11 to the input coupler IN11 in FIG. 5, the incident light L11 may be emitted from the top of the layer structure LS11 to the input coupler IN11.

Figure 6:
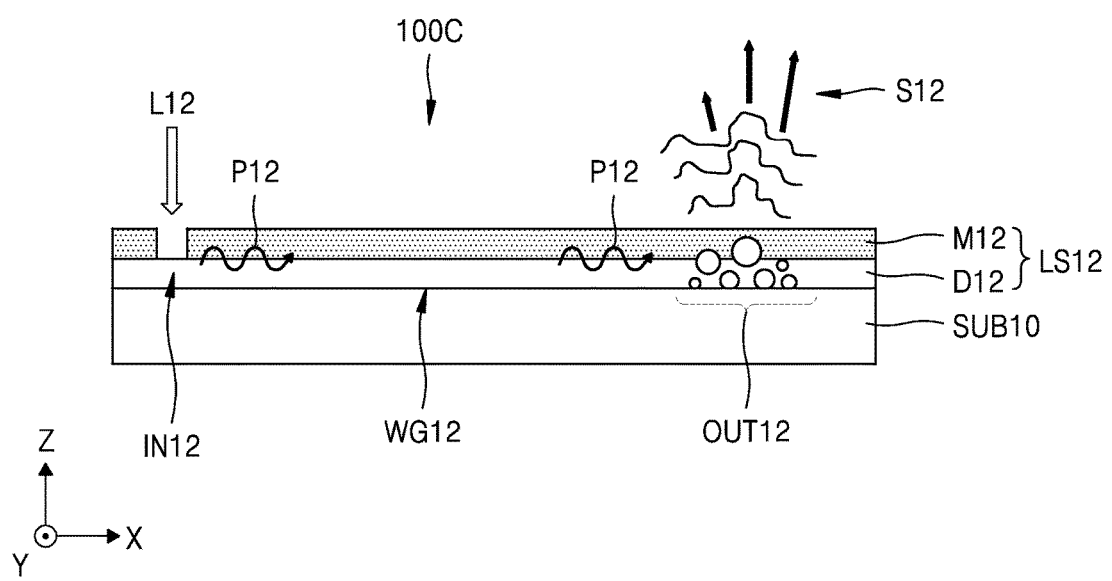
FIG. 6 is a cross-sectional view illustrating an authentication structure for authenticating an object, according to another exemplary embodiment.

According to another exemplary embodiment, positions of the metal layer M11 and the dielectric layer D11 of FIG. 5 may be changed, as shown in FIG. 6.

Referring to FIG. 6, an authentication structure 100C may include a layer structure LS12 that is a multi-layer structure, and the layer structure LS12 may include a dielectric film D12 and a metal film M12. The metal film M12 may be disposed on the dielectric film D12. An input coupler IN12 may be provided in a first area of the layer structure LS12 and an output coupler OUT12 may be provided in a second area of the layer structure LS12, and a waveguide WG12 may be disposed between the input coupler IN12 and the output coupler OUT12. Configurations of the input coupler IN12 and the output coupler OUT12 may be similar to those of FIG. 5. Also, structures of the input coupler IN12 and the output coupler OUT12 may be modified in various ways, like in FIG. 5.

In the present exemplary embodiment, incident light L12 may be emitted from the top or the bottom of the layer structure LS12 to the input coupler IN12. FIG. 6 illustrates a case where the incident light L12 is emitted from the top of the layer structure LS12. Surface plasmons P12 may be generated by the input coupler IN12 due to the incident light L12, and a speckle pattern S12 may be generated and output due to the surface plasmons P12 that are transmitted to the output coupler OUT12.

Figure 7:
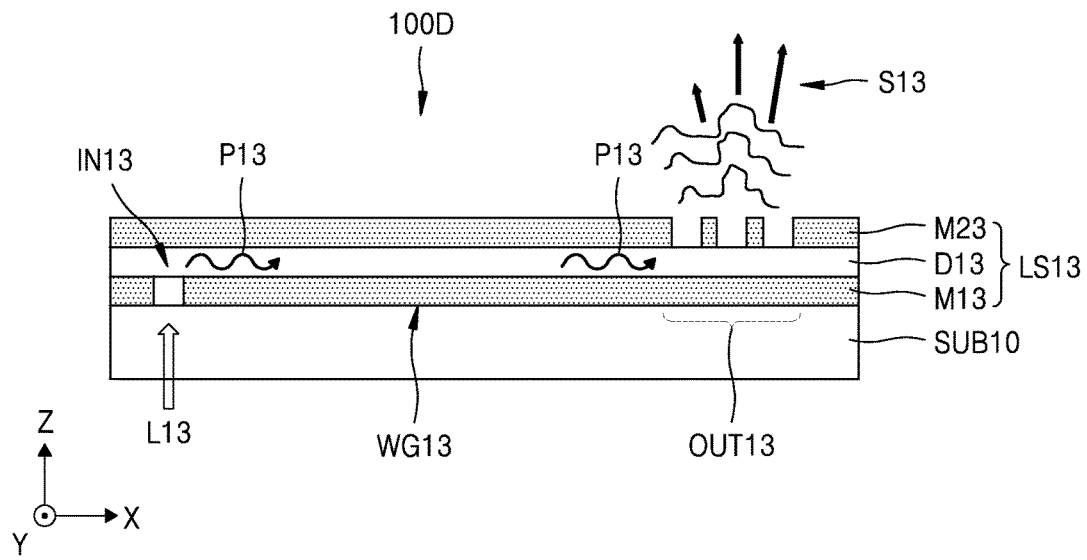
FIG. 7 is a cross-sectional view illustrating an authentication structure for authenticating an object, according to another exemplary embodiment.

FIG. 7 is a cross-sectional view illustrating an authentication structure 100D for authenticating an object, according to another exemplary embodiment.

Referring to FIG. 7, the authentication structure 100D may include a layer structure LS13 that is a multi-layer structure. The layer structure LS13 may include a first metal film M13, a dielectric film D13, and a second metal film M23. The dielectric film D13 may be disposed between the first metal film M13 and the second metal film M23. The dielectric film D13 may be an insulating film. Accordingly, the authentication structure 100D may have a metal-insulator-metal (MIM) structure.

An input coupler IN13 may be provided in a first area of the layer structure LS13 and an output coupler OUT13 may be provided in a second area of the layer structure LS13. The input coupler IN13 may be formed in at least one selected from the first metal film M13 and the dielectric film D13. FIG. 7 illustrates a case where the input coupler IN13 is formed in the first metal film M13. The input coupler IN13 may include, for example, at least one from among a slit or a slot. A portion of the second metal film M23 corresponding to the input coupler IN13 may have a continuous layer structure and may cover the top of the input coupler IN13. The output coupler OUT13 may be formed in at least one selected from the first metal film M13, the dielectric film D13, and the second metal film M23. FIG. 7 illustrates a case where the output coupler OUT13 is formed in the second metal film M23. The output coupler OUT13 may include an optical scatterer, and the optical scatterer may include, for example, a plurality of slits or slots. A portion of the layer structure LS13 between the input coupler IN13 and the output coupler OUT13 may be a waveguide WG13.

When incident light L13 is emitted to the input coupler IN13, surface plasmons P13 may be generated by the input coupler IN13 due to the incident light L13 and may be transmitted to the output coupler OUT13 through the waveguide WG13. A speckle pattern S13 may be generated and output by the output coupler OUT13 due to the surface plasmons P13. The incident light L13 may be coherent light, for example, laser light, and the surface plasmons P13 may be coherent waves. Although the surface plasmons P13 propagate in the dielectric film D13 in FIG. 7, the surface plasmons P13 may actually mainly move through an interface between the first metal film M13 and the dielectric film D13 and an interface between the second metal film M23 and the dielectric film D13.

Because the second metal film M23 covers the top of the input coupler IN13 in the present exemplary embodiment, the incident light L13 may be suppressed or prevented from being transmitted to the top of the input coupler IN13 through the second metal film M23. Accordingly, the speckle pattern S13 may be prevented or minimized from being affected by light transmitted to the top of the input coupler IN13 through the second metal film M23.

Configurations of the input coupler IN13 and the output coupler OUT13 of FIG. 7 are exemplary and various modifications may be made. The input coupler IN13 and the output coupler OUT13 may be similar to the input couplers IN11 and IN12 and the output couplers OUT11 and OUT12 of FIGS. 5 and 6. Also, in FIG. 7, the input coupler IN13 may be formed in the second metal film M23 instead of the first metal film M13. Accordingly, a direction in which the incident light L13 is emitted may also be changed. The incident light L13 may be emitted from the top of the layer structure LS13 to the input coupler IN13.

Figure 8:
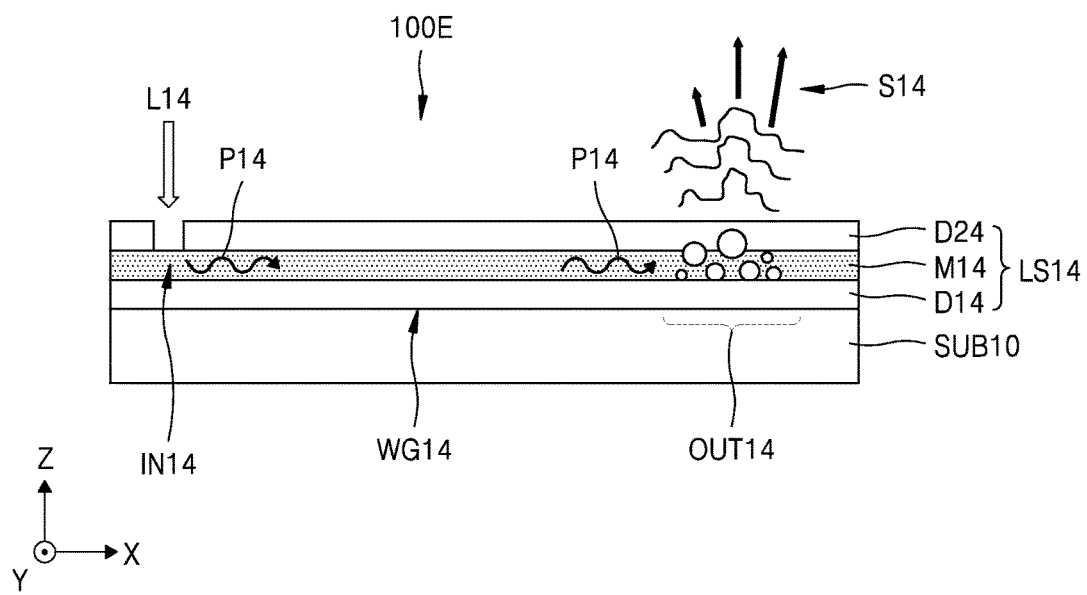
FIG. 8 is a cross-sectional view illustrating an authentication structure for authenticating an object, according to another exemplary embodiment.

FIG. 8 is a cross-sectional view illustrating an authentication structure 100E for authenticating an object, according to another exemplary embodiment.

Referring to FIG. 8, the authentication structure 100E may include a layer structure LS14 that is a multi-layer structure. The layer structure LS14 may include a first dielectric film D14, a metal film M14, and a second dielectric film D24. The metal film M14 may be disposed between the first dielectric film D14 and the second dielectric film D24. The first and second dielectric films D14 and D24 may be insulating films. Accordingly, the authentication structure 100E may have an insulator-metal-insulator (IMI) structure.

An input coupler IN14 may be provided in a first area of the layer structure LS14 and an output coupler OUT14 may be provided in a second area of the layer structure LS14. The input coupler IN14 may be formed in at least one selected from the first dielectric film D14, the metal film M14, and the second dielectric film D24. The input coupler IN14 may include, for example, at least one from among a slit or a slot. The output coupler OUT14 may be formed in at least one selected from the first dielectric film D14, the metal film M14, and the second dielectric film D24. FIG. 8 illustrates a case where the output coupler OUT14 is formed in the metal film M14 and the second dielectric film D24. The output coupler OUT14 may include an optical scatterer, and the optical scatterer may include at least one selected from a slit, a slot, a spherical element, and a rod-type element. FIG. 8 illustrates a case where the optical scatterer includes a plurality of spherical elements. The plurality of spherical elements may have non-uniform sizes and may be randomly arranged. A portion of the layer structure LS14 between the input coupler IN14 and the output coupler OUT14 may be a waveguide WG14.

Surface plasmons P14 may be generated by the input coupler IN14 due to the incident light L14 and may be transmitted to the output coupler OUT14 through the waveguide WG14. A speckle pattern S14 may be generated and output by the output coupler OUT14 through the waveguide WG14. The incident light L14 may be coherent light, for example, laser light, and the surface plasmons P14 may be coherent waves. Although the surface plasmons P14 propagate in the metal film M14 in FIG. 8, the surface plasmons P14 may actually mainly move through an interface between the first dielectric film D14 and the metal film M14 and an interface between the second dielectric film D24 and the metal film M14.

In the present exemplary embodiment, the incident light L14 may be emitted from the top of the layer structure LS14 to the input coupler IN14. The speckle pattern S14 may be detected over the layer structure LS14. Accordingly, a light source for generating the incident light L14 and a detector for detecting the speckle pattern S14 may be located in the same direction in relation to the authentication structure 100E. However, a direction in which the incident light L14 is emitted may be changed. For example, the incident light L14 may be emitted from the bottom of the layer structure LS14 to the input coupler IN14.

Configurations of the input coupler IN14 and the output coupler OUT14 of FIG. 8 are exemplary and various modifications may be made. The input coupler IN14 and the output coupler OUT14 may be similar to the input couplers IN11 through IN13 and the output couplers OUT11 through OUT13 of FIGS. 5 through 7. Also, in FIG. 8, the first dielectric film D14 or the second dielectric film D24 may not be provided. When the second dielectric film D24 is not provided, the input coupler IN14 may be formed in at least one from among the first dielectric film D14 or the metal film M14.

In the authentication structures 100A through 100E of FIGS. 5 through 8, the metal films M11, M12, M13, M14, and M23 may each have a thickness ranging from, for example, several nm to several mm, or a thickness ranging from, for example, tens of nm to hundreds of nm. Also, the dielectric films D11, D12, D13, D14, and D24 may each have a thickness, for example, equal to or greater than several nm.

FIGS. 9 through 14 are cross-sectional views illustrating various output couplers that may be used in an authentication structure, according to exemplary embodiments.

Figure 9:
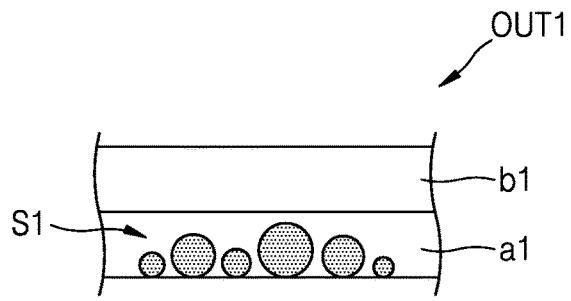
FIGS. 9 through 14 are cross-sectional views illustrating various output couplers that may be used in an authentication apparatus, according to exemplary embodiments.

Referring to FIG. 9, an output coupler OUT1 may include a first layer a1 and a second layer b1, and a plurality of spherical elements S1 may be provided in the first layer a1.

Figure 10:
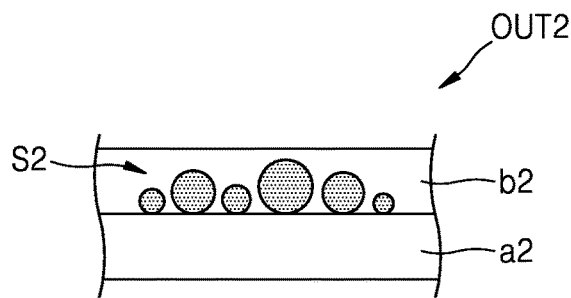

Referring to FIG. 10, an output coupler OUT2 may include a first layer a2 and a second layer b2, and a plurality of spherical elements S2 may be provided in the second layer b2.

Figure 11:
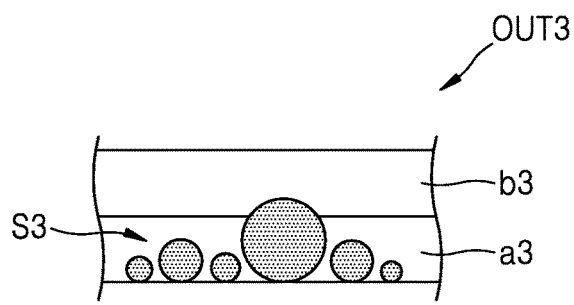

Referring to FIG. 11, an output coupler OUT3 may include a first layer a3 and a second layer b3, a plurality of spherical elements S3 may be provided in the first layer a3, and at least some of the plurality of spherical elements S3 may protrude toward or into the second layer b3.

Figure 12:
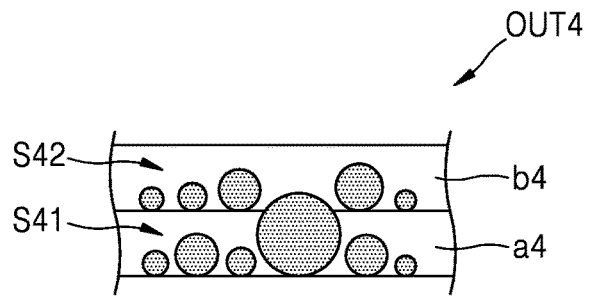

Referring to FIG. 12, an output coupler OUT4 may include a first layer a4 and a second layer b4, a plurality of first spherical element S41 may be provided in the first layer a4, and a plurality of second spherical elements S42 may be provided in the second layer b4. In this case, at least some of the plurality of first spherical elements S41 may protrude toward or into the second layer b4.

Figure 13:
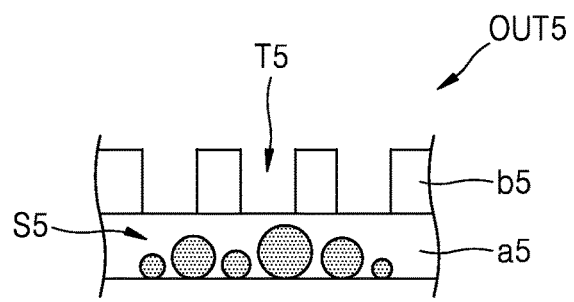

Referring to FIG. 13, an output coupler OUT5 may include a first layer a5 and a second layer b5, a plurality of spherical elements S5 may be provided in the first layer a5, and a plurality of slots T5 may be provided in the second layer b5.

Figure 14:
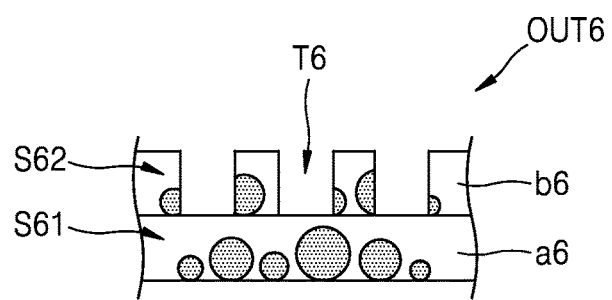

Referring to FIG. 14, an output coupler OUT6 may include a first layer a6 and a second layer b6, a plurality of first spherical elements S61 may be provided in the first layer a6, and a plurality of second spherical elements S62 may be provided in the second layer b6. Also, a plurality of slots T6 may be formed in the second layer b6. The output couplers OUT5 of FIG. 13 and OUT6 of FIG. 14 may be obtained by combining spherical elements and slots.

Although the output couplers OUT1 through OUT6 are configured by providing spherical elements, or both spherical elements and slits in two material layers, that is, the first and second layers a1 through a6 and b1 through b6, in FIGS. 9 through 14, the output couplers OUT1 through OUT6 are exemplary and other various modifications may be made. For example, an output coupler may be configured by combining in various ways rod-type elements, spherical elements, slits, and slots in a single-layer structure or a multi-layer structure including three layers or more.

The authentication structures 100A through 100E of FIGS. 1 through 14 may be disposed on an object (e.g., a device or a product) and may be used to authenticate the object. A positional relationship between each of the authentication structures 100A through 100E and the object will be briefly explained with reference to FIGS. 15 through 17.

Figure 15:
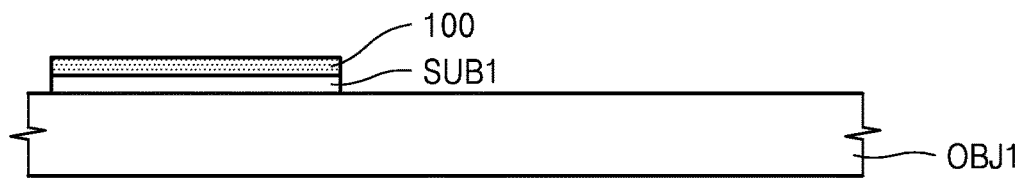
FIGS. 15 through 17 are cross-sectional views for explaining a positional relationship between an authentication structure and an object, according to exemplary embodiments.

As shown in FIG. 15, an authentication structure 100 may be disposed on an object OBJ1. In this case, the authentication structure 100 may be disposed on a substrate SUB1, and then the authentication structure 100 and the substrate SUB1 may be disposed on the object OBJ1. Accordingly, the substrate SUB1 may be disposed between the object OBJ1 and the authentication structure 100. The object OBJ1 may be a device or a product. The substrate SUB1 may correspond to the substrate SUB10 of FIG. 1.

Figure 16:
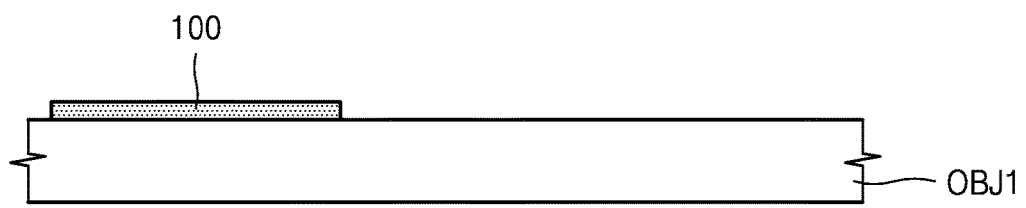

According to another exemplary embodiment, as shown in FIG. 16, the authentication structure 100 may be directly formed on the object OBJ1. That is, a layer structure may be formed on the object OBJ1 without using the substrate SUB1 (see FIG. 15), and then the authentication structure 100 may be formed from the layer structure.

Figure 17:
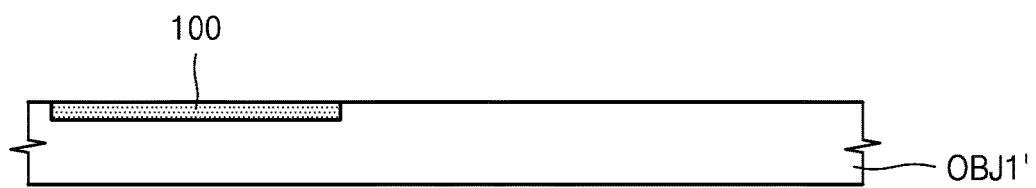

According to another exemplary embodiment, as shown in FIG. 17, the authentication structure 100 may be embedded in an object OBJ1'. For example, a groove may be formed in a surface of the object OBJ1', and then the authentication structure 100 may be inserted into the groove.

Although the authentication structure 100 is simply illustrated in FIGS. 15 through 17, the authentication structure 100 may be any of the authentication structures 100A through 100E of FIGS. 1 through 14 or a modified structure thereof. Also, structures of FIGS. 15 through 17 may each be an apparatus or a product including the authentication structure 100.

The authentication structure 100 of FIGS. 15 through 17 may be used along with a 'protective layer' that is formed on the authentication structure 100. The protective layer will be explained below with reference to FIGS. 18 through 20.

Figure 18:
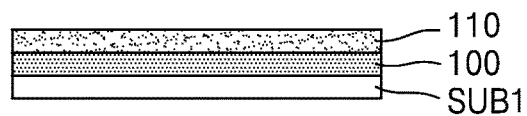
FIGS. 18 through 20 are cross-sectional views illustrating cases where a protective layer is disposed on an authentication structure, according to exemplary embodiments.

As shown in FIG. 18, the authentication structure 100 may be disposed on the substrate SUB1 and a protective layer 110 may be disposed on the authentication structure 100. The protective layer 110 may be an insulating layer and a coating layer. A structure of FIG. 18 may be applied to an object.

Figure 19:
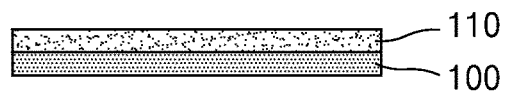

The substrate SUB1 may be omitted from the structure of FIG. 18, as shown in FIG. 19. A structure of FIG. 19 may be applied to an object.

Figure 20:
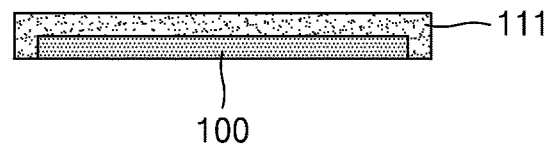

In FIG. 19, the protective layer 110 may be modified to cover not only a top surface of the authentication structure 100 but also side surfaces of the authentication structure 100, as shown in FIG. 20. Referring to FIG. 20, a protective layer 111 is provided to cover both the top surface and the side surfaces of the authentication structure 100. A structure of FIG. 20 may be applied to an object.

Figure 21:
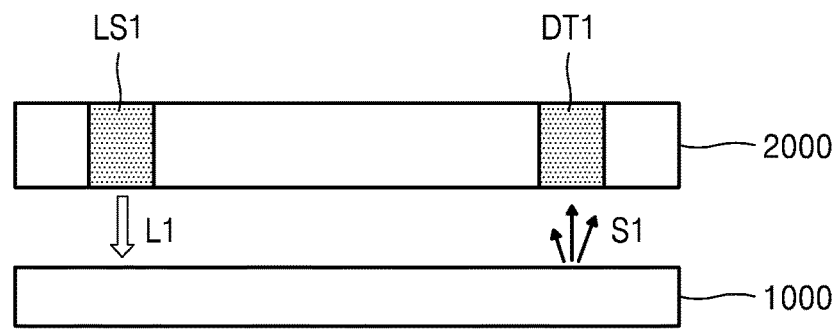
FIG. 21 is a cross-sectional view illustrating an authentication apparatus according to an exemplary embodiment.

FIG. 21 is a cross-sectional view illustrating an authentication apparatus according to an exemplary embodiment.

Referring to FIG. 21, the authentication apparatus of the present exemplary embodiment may include an object 1000 which includes an authentication structure, and an optical pickup 2000 which corresponds to the object 1000. The authentication structure that is included in the object 100 may be the same as or similar to the authentication structure of any of FIGS. 1 through 20. The optical pickup 2000 may include a light source LS1 that emits incident light L1 to an input coupler of the authentication structure and a detector DT1 that detects a speckle pattern S1 output from an output coupler of the authentication structure. Although the input coupler and the output coupler are not specifically shown in FIG. 21, the input coupler and the output coupler may have configurations that are the same as or similar to those of the input coupler and the output coupler of any of FIGS. 1 through 14. The incident light L1 that is generated by the light source LS1 may be coherent light and the coherent light may be laser light. In this case, the light source LS1 may be a laser source. The detector DT1 may include a photodiode, or may include an imaging device such as a charge-coupled device (CCD) or a complementary metal-oxide-semiconductor (CMOS) image sensor. The detector DT1 may function as a camera.

In FIG. 21, the light source LS1 and the detector DT1 may be located in the same direction with respect to the object 1000 including the authentication structure. As shown in FIG. 21, both the light source LS1 and the detector DT1 may be disposed over the object 1000. However, if necessary, both the light source LS1 and the detector DT1 may be disposed under the object 1000.

Figure 22:
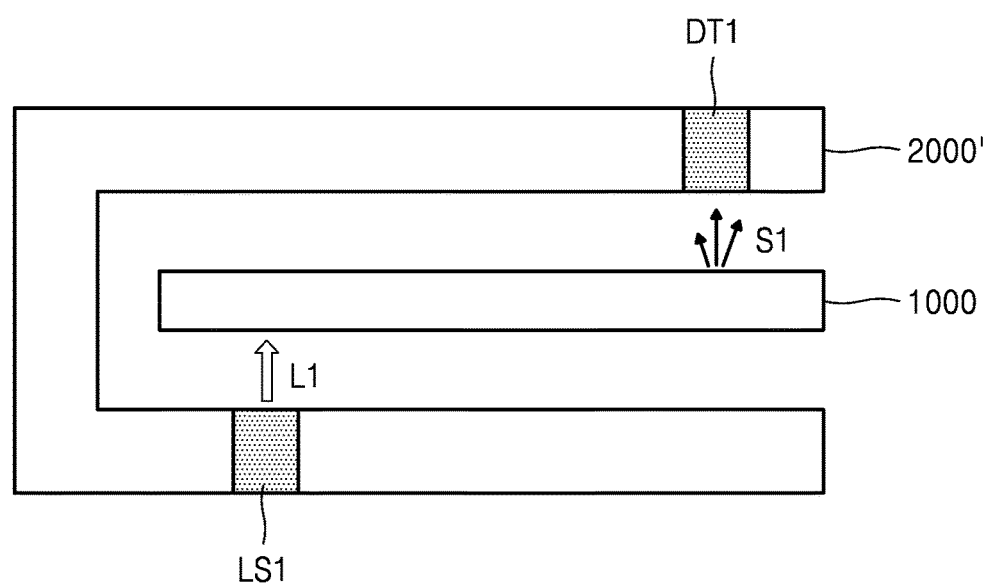
FIG. 22 is a cross-sectional view illustrating an authentication apparatus according to an exemplary embodiment.

According to another exemplary embodiment, the light source LS1 and the detector DT1 of the optical pickup 2000 may be located in different directions with respect to the object 1000, as shown in FIG. 22.

Referring to FIG. 22, the light source LS1 of an optical pickup 2000' may be disposed under the object 1000 and the detector DT1 may be disposed over the object 1000. Alternatively, the light source LS1 may be disposed over the object 1000 and the detector DT1 may be disposed under the object 1000.

The authentication apparatuses of FIGS. 21 and 22 may be understood in relation to the authentication structures 100A through 100E of FIGS. 1 through 8. For example, the authentication structures 100A, 100C, and 100E of FIGS. 1, 6, and 8, respectively, may be applied to the authentication apparatus of FIG. 21 and the authentication structures 100A, 100B, and 100D of FIGS. 2, 5, and 7, respectively, may be applied to the authentication apparatus of FIG. 22.

Figure 23:
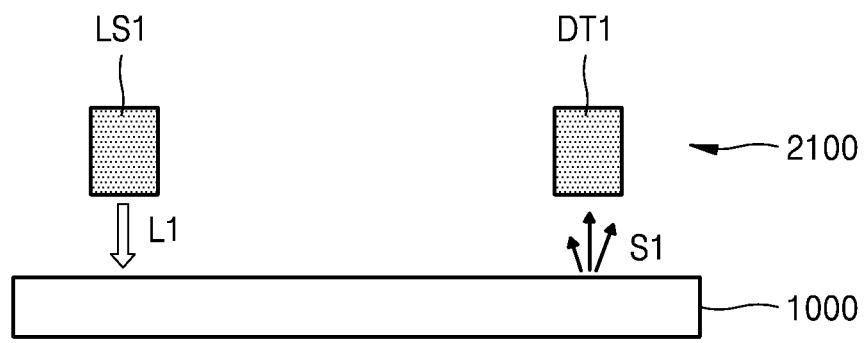
FIG. 23 is a cross-sectional view illustrating an authentication apparatus according to an exemplary embodiment.

According to another exemplary embodiment, the light source LS1 and the detector DT1 may be separately used, without being integrated into one body, as shown in FIG. 23.

Referring to FIG. 23, the light source LS1 and the detector DT1 that are separated from each other may be disposed over the object 1000 including the authentication structure. Even in this case, the light source LS1 and the detector DT1 may constitute one optical pickup 2100. Alternatively, the detector DT1 itself may function as the optical pickup 2100.

Figure 24:
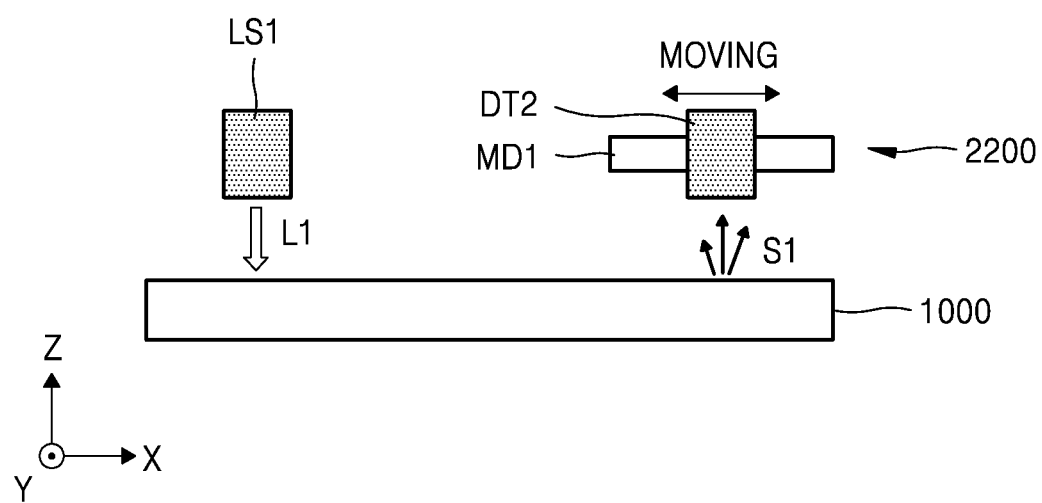
FIG. 24 is a cross-sectional view illustrating an authentication apparatus according to an exemplary embodiment.

According to another exemplary embodiment, the detector DT1 of FIG. 23 may be used along with a 'mover', as shown in FIG. 24.

Referring to FIG. 24, the light source LS1 and a detector DT2 that are separated from each other may be disposed over the object 1000 including the authentication structure. The detector DT2 may be provided on a mover MD1 and may be moved by the mover MD1. The mover MD1 may be referred to as a 'moving stage'. The mover MD1 may use, for example, a piezoelectric effect. In this case, a precise position movement may be made. The detector DT2 may be moved in at least one from among an X-axis direction or a Y-axis direction by the mover MD1. The detector DT2 may obtain data about the speckle pattern S1 by scanning the speckle pattern S1. The light source LS1, the detector DT2, and the mover MD1 may constitute one optical pickup 2200. Alternatively, the detector DT2 and the mover MD1 may constitute one optical pickup 2200.

In FIGS. 23 and 24, the light source LS1 may be disposed under the object 1000. Alternatively, the light source LS1 may be disposed over the object 1000 and the detectors DT1 and DT2 may be disposed under the object 1000.

Figure 25:
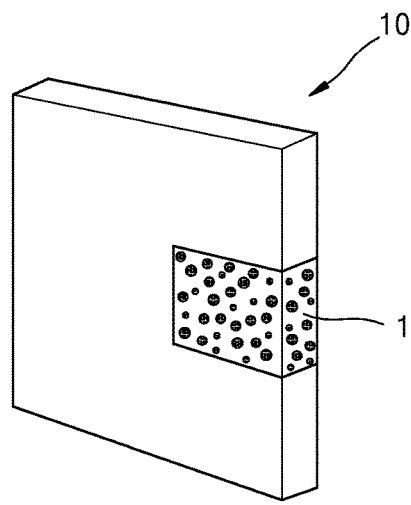
FIG. 25 is a perspective view illustrating a physical unclonable function (PUF) structure according to a comparative example.

FIG. 25 is a perspective view illustrating a PUF structure 10 according to a comparative example.

Referring to FIG. 25, the PUF structure 10 according to the comparative example may include a token 1. The token 1 may have a structure in which glass beads are randomly distributed in a specific material layer. A light source for emitting light to the token 1 may be disposed on a side of the PUF structure 10 and a detector (not shown) for detecting light transmitted through the token 1 may be disposed on the other side of the PUF structure 10. In this case, the light source, the token 1, and the detector may be aligned in a straight line. When a method using the token 1 that is formed by randomly distributing the glass beads is used, an image unfortunately varies according to a direction in which the light is emitted to the token 1 and positions of the token 1 and the detector, thereby reducing stability or reliability. Accordingly, although the method may provide a result that may be acceptable in a laboratory or the like having a precision of several μm, it may be difficult to popularize or commercialize the method. Also, because the token 1 has a large size and a relatively bulky measurement system is required, applications are limited and usability is reduced.

However, in the authentication structure according to the one or more of the exemplary embodiments, once a structure of an input coupler is determined, coherent waves (e.g., surface plasmons) having the same wavenumber may be generated irrespective of an angle at which incident light is emitted. Also, the coherent waves (e.g., the surface plasmons) that are generated by the input coupler are transmitted to an output coupler and an interference pattern (that is, a speckle pattern) is output from the output coupler. Because the input coupler and the output coupler are fixed and the interference pattern (e.g., the speckle pattern) is output due to the coherent waves (e.g., the surface plasmons) that are transmitted to the output coupler, the interference pattern (e.g., the speckle pattern) may be determined by the authentication structure and may not be affected by an angle at which incident light is emitted or a position of a light source. Accordingly, the coherent waves (e.g., the surface plasmons) may be stably and uniformly generated irrespective of the angle at which the incident light is emitted, and thus the interference pattern (e.g., the speckle pattern) may be stably and uniformly output. Hence, the authentication structure according to the one or more of the exemplary embodiments may have desirable stability or reliability and may be more easily popularized or commercialized.

Also, the authentication structure according to the one or more of the exemplary embodiments may be manufactured to have a very small size. Because the input coupler and the output coupler may be formed in a layer structure that is a single-layer or multi-layer structure by using a semiconductor device manufacturing technology, the authentication structure having a very small size may be easily manufactured. For example, the authentication structure may be manufactured to have a size less than 100 μm×100 μm or a size less than tens of μm×tens of μm, and may be manufactured to have a very small thickness. The authentication structure may be easily applied to any device requiring authentication. The authentication structure may be formed while a device or a product is manufactured, or the authentication structure may be separately manufactured and then may be attached or otherwise bonded to a device or a product. In the latter case, the authentication structure may be of a sticker type or a band type. In this regard, the authentication structure according to the one or more of the exemplary embodiments may be easily popularized or commercialized.

In addition, the authentication structure according to the one or more of the exemplary embodiments has a small size, and thus may also be applied to a flexible device. For example, the flexible device may have a local portion that is not bent and the authentication structure may be provided on the local portion.

In addition, because an optical pickup corresponding to the authentication structure according to the one or more of the exemplary embodiments may also be manufactured to have a relatively small size and a technology of driving the optical pickup is relatively simple, the authentication structure may be easily authenticated by using a compact reader.

Figure 26:
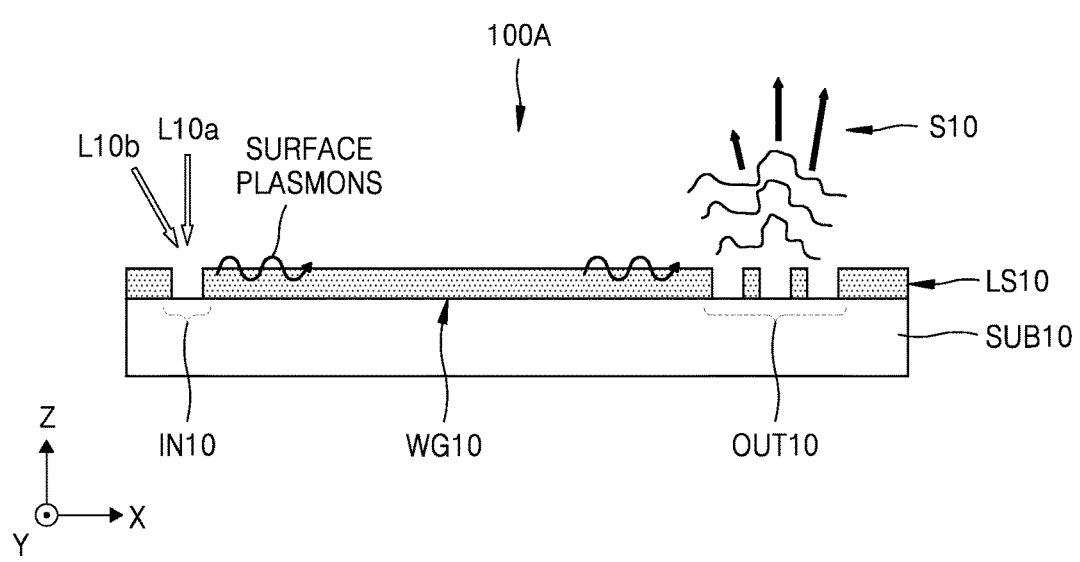
FIG. 26 is a cross-sectional view for explaining an effect of angles of incident light on an operation of an authentication structure, according to an exemplary embodiment.

FIG. 26 is a cross-sectional view for explaining an effect of angles of incident light L10a and L10b on an operation of the authentication structure 100A, according to an exemplary embodiment.

Referring to FIG. 26, assuming that the incident light L10a and L10b having the same wavelength are used, even when angles (hereinafter, referred to incidence angles) at which the incident light L10a and L10b are incident are changed, a wavenumber of generated surface plasmons may be constant. When a structure and a material of the input coupler IN10 are fixed, a correlation between a wavelength of incident light incident on the input coupler IN10 and a wavenumber of surface plasmons that are generated by the input coupler IN10 may be accordingly determined. Accordingly, even when an incidence angle of the incident light is changed, if the wavelength is fixed, the wavenumber of the generated surface plasmons may be constant. That is, in FIG. 26, a wavenumber of surface plasmons that are generated due to the first incident L10a and a wavenumber of surface plasmons that are generated due to the second incident light L10b may be the same. Even when incidence angles of the incident light L10a and L10b are different from each other, surface plasmons having the same wavenumber may be generated, and thus the speckle pattern S10 having the same shape may be output.

Intensities of surface plasmons that are generated may be slightly different from each other according to the incidence angles of the incident light L10a and L10b. Although an intensity of surface plasmons is changed, however, a contrast ratio of the speckle pattern S10 may be constant. When the speckle pattern S10 is detected, because the speckle pattern S10 may be detected based on a contrast ratio, detected data may be constant although there is a change in the intensity of the surface plasmons.

Figure 27:
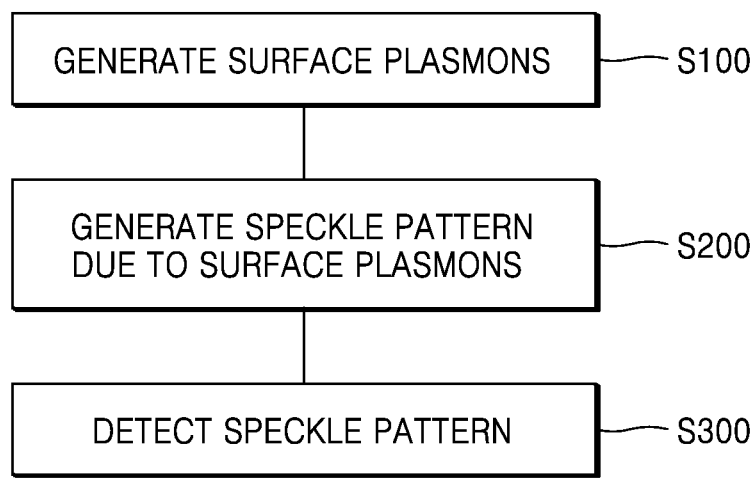
FIG. 27 is a flowchart for explaining an authentication method according to an exemplary embodiment.

FIG. 27 is a flowchart for explaining an authentication method according to an exemplary embodiment. The authentication method of FIG. 27 is related to the authentication structure and the apparatus or the system including the authentication structure of FIGS. 1 through 24. Accordingly, the authentication method of FIG. 27 may be understood based on the description of FIGS. 1 through 24.

Referring to FIG. 27, the authentication method of the present exemplary embodiment may include operation S100 in which surface plasmons are generated, operation S200 in which a speckle pattern is produced by the surface plasmons, and operation S300 in which the speckle pattern is detected.

The authentication method may be performed by using the authentication structure and the apparatus or the system including the authentication structure of FIGS. 1 through 24. The authentication structure may include an input coupler and an output coupler that are spaced apart from each other and a waveguide that is disposed between the input coupler and the output coupler.

The input coupler may generate the surface plasmons. In order for the input coupler to generate the surface plasmons, incident light may be emitted to the input coupler. The incident light may be coherent light. For example, the incident light may be laser light. The incident light (e.g., laser light) may be emitted to the input coupler by using a light source (e.g., a laser source). The speckle pattern produced by the surface plasmons may be output from the output coupler. The speckle pattern may be detected by using a detector. The waveguide may function to transmit the surface plasmons from the input coupler to the output coupler.

According to exemplary embodiments, the light source for emitting the incident light and the detector for detecting the speckle pattern may be located in the same direction with respect to the authentication structure, as shown for example in FIGS. 21, 23, and 24. Alternatively, the light source for emitting the incident light and the detector for detecting the speckle pattern may be located in different directions with respect to the authentication structure, as shown for example in FIG. 22.

In the authentication method of FIG. 27, the 'surface plasmons' may be coherent waves. Also, the 'speckle pattern' may be an interference pattern. Accordingly, the authentication method according to an exemplary embodiment may include an operation of generating coherent waves, an operation of generating an interference pattern due to the coherent waves, and an operation of detecting the interference pattern. In this case, the coherent waves may be surface plasmons and the interference pattern may be a speckle pattern.

The authentication structure, the authentication method, and the apparatus using the authentication structure and the authentication method according to the one or more of the exemplary embodiments may be applied to various objects (e.g., devices, furniture, and products) for security purposes. For example, the authentication structure, the authentication method, and the apparatus may be applied to a smart card, a memory device (e.g., a memory stick), a storage medium, or a component of an individual device. The authentication structure, the authentication method, and the apparatus may also be applied to a mobile communication device such as a mobile phone, an Internet of Things (IOT) device, a radio-frequency identification (RFID) product or device, and a home networking system. In an apparatus or a system having openness and portability such as a mobile phone, because there are many security concerns and a software-based security technology has many limitations, a hardware-based security technology may be desirable. The authentication structure and the authentication method according to the one or more of the exemplary embodiments may be usefully applied to the hardware-based security technology. As for a mobile phone, the authentication structure and the authentication method according to the one or more of the exemplary embodiments may be used for system security, chip-level security, and data storage security purposes. Also, as for a mobile trusted module (MTM), the authentication structure and the authentication method according to the one or more of the exemplary embodiments may be used for physical security purposes. Also, the authentication structure and the authentication method according to the one or more of the exemplary embodiments may be used to verify the integrity of an individual device or a component of the individual device. The above various applications are exemplary and the authentication structure and the authentication method according to the one or more of the exemplary embodiments may be applied to any device requiring hardware-based authentication.

Because the authentication structure and the authentication method according to the one or more of the exemplary embodiments use an optical method, the authentication structure and the authentication method may be strong against various physical attacks (for example, reverse engineering, side channel attack, light emission, and fault injection). Also, because the authentication structure and the authentication method according to the one or more of the exemplary embodiments may provide a constant output by simply emitting light to an input coupler and are not greatly affected by a voltage, current, or heat, the authentication structure and the authentication method may have excellent system stability. Also, the authentication structure and the authentication method according to the one or more of the exemplary embodiments may be strong against a high output complexity and physical duplication. Also, because the authentication structure having a small size may be easily manufactured by using a general semiconductor device manufacturing technology, production costs may be reduced and the authentication structure may be easily applied to various products or devices.

While several exemplary embodiments have been particularly shown and described, they are provided for the purposes of illustration and it will be understood by those of ordinary skill in the art that various modifications and equivalent other exemplary embodiments can be made. For example, it will be understood by one of ordinary skill in the art that a configuration of an authentication structure of any of FIGS. 1 through 20 and a configuration of an authentication apparatus or a system of any of FIGS. 21 through 24 may be modified in various ways. Also, it will also be understood that an authentication method of FIG. 27 may be modified in various ways.

What is claimed is:

1. An authentication apparatus for authenticating an object, the authentication apparatus comprising:
   a layered structure comprising:
      an input coupler, formed in a first area and configured to receive incident light and generate surface plasmons from the incident light; and
      an output coupler, formed in a second area and configured to output a speckle pattern based on the surface plasmons, wherein the output coupler comprises an optical scatterer.

2. The authentication apparatus of claim 1, wherein the authentication apparatus further comprises:
   a waveguide configured to transmit to the output coupler the surface plasmons generated by the input coupler.

3. The authentication apparatus of claim 1, wherein the first area and the second area are spaced apart from each other in an in-plane direction of the layer structure.

4. The authentication apparatus of claim 1, wherein the input coupler comprises a slot formed in the first area of the layer structure.

5. The authentication apparatus of claim 1, wherein the optical scatterer comprises at least one among a slot, a spherical element, and a rod-type element, configured to scatter light.

6. The authentication apparatus of claim 1, wherein the optical scatterer comprises a plurality of scattering elements, each scattering element of the plurality of scattering elements being a nanoscale size or a microscale size.

7. The authentication apparatus of claim 1, wherein the authentication apparatus comprises a metal film,
   wherein the input coupler is formed in the first area on the metal film, and the output coupler is formed in the second area in the metal film.

8. The authentication apparatus of claim 1, wherein the layered structure is a multi-layer structure comprising a metal film and a dielectric film.

9. The authentication apparatus of claim 8, wherein the dielectric film is formed on the metal film and is configured to protect the metal film.

10. The authentication apparatus of claim 1, wherein the layered structure is a multi-layer structure comprising a first metal film, a second metal film, and a dielectric film disposed between the first metal film and the second metal film.

11. The authentication apparatus of claim 10, wherein the dielectric film and the second metal film are sequentially disposed on the first metal film,
   wherein the input coupler is formed in at least one among the first metal film and the dielectric film.

12. The authentication apparatus of claim 1, wherein the layered structure is a multi-layer structure comprising a first dielectric film, a second dielectric film, and a metal film disposed between the first dielectric film and the second dielectric film.

13. The authentication apparatus of claim 1, wherein the authentication apparatus is formed on the object, and
   wherein a substrate is further provided between the authentication apparatus and the object.

14. An apparatus comprising:
an authentication structure configured to authenticate an object,
wherein the authentication structure comprises:
    a layered structure comprising:
        an input coupler, formed in a first area;
        an output coupler, formed in a second area spaced apart from the input coupler; and
        a waveguide disposed between the input coupler and the output coupler,
        wherein the output coupler comprises an optical scatterer configured to output an interference pattern produced by coherent waves that are guided along the waveguide from the input coupler to the output coupler.

15. The apparatus of claim 14, wherein the coherent waves comprise surface plasmons.

16. The apparatus of claim 14, wherein the interference pattern comprises a speckle pattern.

17. A method of authenticating an object, the authentication method comprising:
irradiating an input coupler of a layered structure, wherein the input coupler is formed in a first area of the layered structure and is configured to receive incident light and generate surface plasmons from the incident light;
an output coupler, formed in a second area of the layered structure and comprising an optical scatterer, generating a speckle pattern based on the surface plasmons;
detecting the speckle pattern; and
authenticating the object based on the speckle pattern.

18. The authentication method of claim 17, wherein the layered structure further comprises a waveguide disposed between the input coupler and the output coupler.

19. An authentication apparatus for authenticating an object, the authentication apparatus comprising:
an input coupler configured to receive incident light and generate surface plasmons from the incident light; and
an output coupler configured to output a speckle pattern based on the surface plasmons;
wherein the input coupler and the output coupler are both formed in a same layer of the authentication apparatus.

* * * * *